United States Patent [19]

Horwell et al.

[11] Patent Number: 5,218,123
[45] Date of Patent: Jun. 8, 1993

[54] DIDEHYDROTRYPTOPHAN DERIVATIVES AND PHARMACEUTICAL USE THEREOF

[75] Inventors: David C. Horwell; Martyn C. Pritchard, both of Cambridge, England

[73] Assignee: Warner-Lambert Company, Morris Plains, N.J.

[21] Appl. No.: 837,016

[22] Filed: Feb. 18, 1992

[51] Int. Cl.$^5$ .............. C07D 209/70; C07D 401/12; A61K 31/405; A61K 31/44
[52] U.S. Cl. .................................. 546/273; 548/495
[58] Field of Search ............... 548/495; 514/415, 414; 546/273

[56] References Cited

U.S. PATENT DOCUMENTS 4,814,463  3/1989  Kim .................................. 548/495
4,902,708  2/1990  Kim .................................. 548/494

OTHER PUBLICATIONS

*Regulatory Peptides*, 14:277–291 (1986), R. Schick et al., "Intracerebroventricular injections of cholecystokinin . . .".
*Neuropharmacology*, 26(4):389–300 (1987), R. Hill et al., "Antinociceptive Action of Cholecystokinin Octapeptide . . .".
*Brain Research*, 406:130–135 (1987), B. MacVicar et al., "Inhibition of Synaptic Transmission in the hippocampus . . .".
*Brain Research*, 288:199–211 (1983), G. Roberts et al., "Peptides, The Limbic Lobe and Schizophrenia".
*Neuroscience*, 19(1):181–192 (1986), S. Totterdell et al., "Cholecycystokinin–immunoreactive Boutons in Synaptic . . .".
*Pharmacology, Biochemistry & Behavior*, 30:309–137 (1988), F. Weiss et al., "Opposite Actions of CCK-8 . . .".
*Peptides*, 4:749–753 (1983), L. Schneider et al., "CCK-8 Modulation of Mesolimbic Dopamine: . . .".
*Gastrointestinal Hormones*, (1980), CH. 23, S. Konturek, 529–564, "Gastrointestinal Hormones and Gastric Secretion".
ibid., CH. 22, pp. 507–527, L. Johnson, "Effect of Gastrointestinal Hormones on Growth of Gastrointestinal . . .".
ibid., CH. 30, pp. 729–739, F. Stadil, "Gastrinomas".
*Cancer Research*, 46:1612–1616 (1986), P. Singh, "Role of Gastrin and Gastrin Receptors on the Growth . . .".
*Gastroenterology*, 95:1541–1548 (1988), J. Smith et al., "Effects of Gastrin, Proglumide, and Somatostatin . .".
*British Medical Bulletin*, 38(3):253–258 (1982), G. Dockray, "The physiology of Cholecystokinin in Brain and Gut".
*Gastrointestinal Hormones*, CH. 7 (1980), pp. 169–221, V. Mutt, "Cholecystokinin: Isolation, Structure . . .".
*Life Sciences*, 27:355–368 (1980), J. Morley, "The Neuroendrocrine Control of Appetite: The Role of . . .".
*CCK in the Nervous System*, CH. 7, (1984), pp. 110–127, M. Sheehan et al., "Central Actions of Cholecystokinin . . .".
*Journal of Neurochemistry*, 32:1339–1341 (1979), "Immunochemical evidence of cholecystokinin Octapeptides: Continuous Picomole Injections into the Cerebral . .".
*Journal of Neuroscience*, 8(3):988–1000 (1988), H. Demeulemeester et al., "Heterogeneity of GABAergic . . .".
Goodman and Gilman's *The Pharmacological Basis of Therapeutics*, 7th ed., (1985), pp. 339–371, CH. 17, S. Harvey, "Hypnotics and Sedatives".
*Ann. Rev. Pharmacol. Toxicol.*, 31:469–501 (1991), G. Woodruff, "Cholecystokinin Antagonists".

*Primary Examiner*—David B. Springer
*Attorney, Agent, or Firm*—Elizabeth M. Anderson

[57] ABSTRACT

Novel didehydrotryptophan derivatives useful as agents in the reduction of gastric acid secretion and in the treatment of anxiety, psychoses, and the symptoms of cognitive decline are disclosed. Processes for making the compounds and novel intermediates useful in the processes as well as compositions containing the compounds and methods of using them are also disclosed.

11 Claims, No Drawings

DIDEHYDROTRYPTOPHAN DERIVATIVES AND PHARMACEUTICAL USE THEREOF

BACKGROUND OF THE INVENTION

Agents acting at central cholecystokinin (CCK) receptors induce satiety (Schick, Yaksh, and Go, *Regulatory Peptides* 14:277-291, 1986). They are also expected to act as analgesics (Hill, Hughes, and Pittaway, *Neuropharmacology* 26:289-300, 1987), and as anticonvulsants (MacVicar, Kerrin, and Davison, *Brain Research* 406:130-135, 1987).

Reduced levels of CCK-peptides have been found in the brains of schizophrenic patients compared with controls (Roberts, Ferrier, Lee, Crow, Johnstone, Owens, Bacarese-Hamilton, McGregor, O'Shaughnessey, Polak, and Bloom, *Brain Research* 288:199-211, 1983). It has been proposed that changes in the activity of CCK neurones projecting to the nucleus accumbens may play a role in schizophrenic processes by influencing dopaminergic function (Totterdell and Smith, *Neuroscience* 19:181-192, 1986). This is consistent with numerous reports that CCK peptides modulate dopaminergic function in the basal ganglia and particularly the nucleus accumbens (Weiss, Tanzer, and Ettenberg, *Pharmacology, Biochemistry and Behaviour* 30:309-317, 1988; Schneider, Allpert, and Iversen, *Peptides* 4:749-753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence and CCK peptides can bind to the gastrin receptor of the stomach mucosa and elicit acid secretion in many species including human (Konturek, *Gastrointestinal Hormones*, Ch. 23, pp 529-564, 1980, ed. G. B. J. Glass, Raven Press, NY). Antagonists of the CCK-B receptor would also be expected to be antagonists at the stomach gastrin receptor and this would also be of value for conditions involving excessive acid secretion.

CCK and gastrin peptides have trophic effects on the pancreas and various tissues of the gastrointestinal tract (Johnson, ibid., pp 507-527), actions which are associated with increased DNA and RNA synthesis. Moreover, gastrin secreting cells are associated with certain gastrointestinal tumors as in the Zollinger-Ellison syndrome (Stadil, ibid., pp 729-739), and some colorectal tumors may also be gastrin/CCK dependent (Singh, Walker, Townsend, and Thompson, *Cancer Research* 46:1612, 1986, and Smith, J. P., *Gastroenterology* 95:1541, 1988). Antagonists of CCK/gastrin receptors could therefore be of therapeutic value as antitumor agents.

The cholecystokinin peptides are widely distributed in various organs of the body including the gastrointestinal tract, endocrine glands, and the nerves of the peripheral and central nervous systems. Various biologically active forms have been identified including a 33-amino acid hormone and various carboxyl-terminus fragments of this peptide (e.g., the octapeptide CCK26-33 and the tetrapeptide CCK30-33) (G. J. Dockray, *Br. Med. Bull.* 38(3):253-258, 1982).

The various CCK peptides are thought to be involved in the control of smooth muscle contractility, exocrine and endocrine gland secretion, sensory nerve transmission, and numerous brain functions. Administration of the native peptides causes gall bladder contraction, amylase secretion, excitation of central neurons, inhibition of feeding, anticonvulsive actions, and other behavioral effects (*Cholecystokinin: Isolation, Structure and Functions*, G. B. J. Glass, Ed., Raven Press, New York, 1980, pp 169-221; J. E. Morley, *Life Sciences* 27:355-368, 1980; *Cholecystokinin in the Nervous System*, J. de Belleroche and G. J. Dockray, Ed., Ellis Horwood, Chichester, England, 1984, pp 110-127.)

The high concentrations of CCK peptides in many brain areas also indicate major brain functions for these peptides (G. J. Dockray, *Br. Med. Bull.* 38:(3):253-258, 1982). The most abundant form of brain CCK found is CCK26-33, although small quantities of CCK30-33 exist (Rehfeld and Gotterman, *J. Neurochem.* 32:1339-1341, 1979). The role of central nervous system CCK is not known with certainty, but it has been implicated in the control of feeding (Della-Fera and Baile, *Science* 206:471-473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (H. Demeulemeester et al, *J. Neuroscience* 8:988-1000, 1988). Agents that modify GABA action may have utility as anxiolytic or hypnotic agents (S. C. Harvey, *The Pharmacological Basis of Therapeutics* (7th ed.) 1985, pp 339-371, MacMillan). Thus, agents which modify CCK action may have parallel anxiolytic or hypnotic activities.

CCK receptors are classified into two types: $CCK_A$ and $CCK_B$, both of which are present in the brain (G. N. Woodruff and J. Hughes, *Ann. Rev. Pharmacol.* 31:469-501, 1991).

SUMMARY OF THE INVENTION

The invention relates to novel compounds of the formula

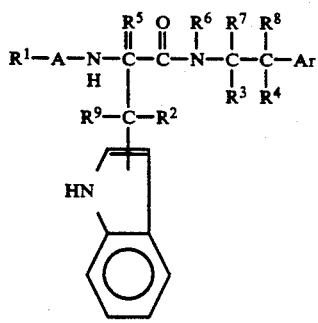

and the pharmaceutically acceptable salts thereof wherein $R^1$, $R^2$, $R^3$, $R^4$, $R^5$, $R^6$, $R^7$, $R^8$, $R^9$, A, and Ar are as defined hereinbelow.

The compounds are also useful as anxiolytics, antipsychotics, especially for treating schizophrenic behavior, as agents in treating disorders of the extrapyramidal motor system, as agents for blocking the trophic and growth stimulating actions of CCK and gastrin, and as agents for treating gastrointestinal motility.

The invention also relates to a pharmaceutical composition for reducing gastric acid secretion containing an effective amount of a compound of Formula I in combination with a pharmaceutically acceptable carrier in unit dosage form effective for reducing gastric acid secretion.

The invention also relates to a method for reducing gastric acid secretion in mammals which comprises administering an effective amount of the composition described above to a mammal in need of such treatment.

The invention also relates to a pharmaceutical composition containing an effective amount of a compound of Formula I in combination with a pharmaceutically acceptable carrier in unit dosage form effective for reducing anxiety.

The invention also relates to a method for reducing anxiety in mammals which comprises administering an effective amount of the composition described above to a mammal in need of such treatment.

The invention also relates to a pharmaceutical composition containing an effective amount of a compound of Formula I in combination with a pharmaceutically acceptable carrier in unit dosage form effective for treating gastrointestinal ulcers.

The invention further relates to a method for treating gastrointestinal ulcers in mammals which comprises administering a composition as described above to a mammal in need of such treatment.

The invention also relates to a pharmaceutical composition containing an effective amount of a compound of Formula I in combination with a pharmaceutically acceptable carrier in unit dosage form effective for treating psychosis, i.e., schizophrenia.

The invention further relates to a method for treating psychosis in mammals which comprises administering a composition as described above to a mammal in need of such treatment.

The invention also relates to a pharmaceutical composition containing a therapeutically effective amount of a compound of Formula I in combination with a pharmaceutically acceptable carrier in unit dosage form effective for treating the symptoms of cognitive disorders.

The invention also relates to a method for treating the symptoms of cognitive decline in a mammal in need of such treatment.

The invention also relates to pharmaceutical compositions effective for stimulating or blocking CCK or gastrin receptors, for altering the activity of brain neurons, for schizophrenia, for treating disorders of the extrapyramidal motor system, for blocking the gastric acid secretory and the trophic and growth stimulating actions of CCK and gastrin, and for treating gastrointestinal motility.

The invention further provides processes for the preparation of compounds of Formula I.

The invention further provides novel intermediates useful in the preparation of compounds of Formula I and also provides processes for the preparation of the intermediates.

DETAILED DESCRIPTION

The didehydrotryptophan derivatives of the present invention are those of formula

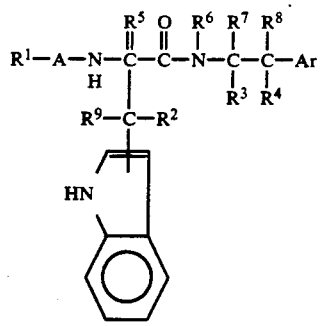

or a pharmaceutically acceptable salt thereof wherein $R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^{11}R^{12}$, and $-(CH_2)_nOR^{11}$ wherein R* is hydrogen or a straight or branched alkyl of from one to six carbon atoms, $R^{11}$ and $R^{12}$ are each independently hydrogen or alkyl of from one to about six carbon atoms and n is an integer of from zero to six;

A is $-(CH_2)_nCO-$, $-SO_2-$, $-NHCO-$, or $-O(CH_2)_nCO-$ wherein n is an integer of from 0 to 6;

$R^2$ and $R^5$ are taken together to form a double bond or to form a ring $-(CH_2)_mX(CH_2)_n$ wherein m is an integer of from 0 to 5, n is as defined above, wherein m and n cannot both be 0 and the sum of m and n is not greater than 8, X is a bond, $-N=N-$ or a heteroatom selected from O, S, or N;

$R^3$ and $R^4$ are each independently hydrogen or $-(CH_2)_{n'}$-B-D wherein n' is an integer of from zero to 3, B is a bond or $-OCO(CH_2)_n-$, $-O(CH_2)_n-$, $-NHCO(CH_2)_n-$, $-CONH(CH_2)_n-$, $-NHCOCH=CH-$, or $-COO(CH_2)_n-$ wherein n is as defined above, and D is $-COOR^{10}$, $-CONH_2$, $-CN$, $-NH_2$, $-OH$, or $-H$ wherein $R^{10}$ is hydrogen or a straight or branched alkyl of from 1 to 6 carbon atoms or $-(CH_2)_nCO_2H$;

$R^6$ is hydrogen or a straight or branched alkyl of from 1 to 6 carbon atoms or $-(CH_2)_nCO_2H$;

$R^7$ and $R^8$ are each independently hydrogen, or can together form a doubly bonded moiety; and $R^9$ is hydrogen, $-C\equiv N$, $-CO_2R_{10}$, $-R_{10}$, $-NR_{10}R_6$, $-SR_{10}$ wherein $R_{10}$ is as defined above;

Ar is a mono- or polycyclic unsubstituted or substituted carbo- or heterocyclic aromatic or hydroaromatic moiety.

The double bond in $R^2$ and $R^5$ above indicates the compound can exist in the E or Z form or as a mixture of E and Z isomers.

Preferred compounds of the present invention are those of Formula I
wherein $R^1$ is adamantyl, endobornyl, methylcyclohexyl, or cyclooctyl;

A is —OCO—, —NHCO—, or —$(CH_2)_nCO$—;

$R^2$ and $R^5$ are taken together to form cyclopropyl or a double bond;

$R^6$ is hydrogen or $CH_2CO_2H$;

$R^3$ and $R^4$ are each independently selected from $CH_2CO_2H$, $NHCO(CH_2)_nCO_2H$, $(CH_2)_nNHCOCH=CHCO_2H$, $CH_2S(O)_pCH_2CO_2H$, wherein p is an integer of from 0 to 2, and n is as defined above;

$R^7$ and $R^8$ are each independently hydrogen or together form a doubly bonded moiety;

$R^9$ is hydrogen, —C≡N, —$CO_2C_2H_5$, or —$CH_3$;

Ar is phenyl, phenyl substituted by halogen, pyridinyl, or cyclohexyl;

$R^2$ and $R^5$ cannot both be hydrogen.

More preferred compounds of the instant invention are those of Formula I wherein $R^1$ is 2-adamantyl, 1-S-endobornyl, or 2-methylcyclohexyl;

A is —OCO— or —NHCO—;

$R^2$ and $R^5$ taken together form a double bond;

$R^3$ and $R^4$ are each independently hydrogen, $CH_2CO_2H$, $NHCO(CH_2)_2CO_2H$, or $CH_2NHCOCH=CHCO_2H$;

$R^6$ is hydrogen;

$R^7$ and $R^8$ are hydrogen or taken together form a double bond;

$R^9$ is hydrogen, methyl, or C≡N; and

Ar is phenyl or pyridinyl.

Especially preferred compounds of the instant invention named:

Carbamic acid, [1 (1H-indol-3-ylmethylene)-2-oxo-2-[(2-phenylethyl)amino]ethyl], tricyclo [3.3.1.1$^{3,7}$]dec-2-yl ester, (Z)-;

(Z)-N-[α,β-Didehydro-N-[(tricyclo [3.3.1.1$^{3,7}$]dec-2-yloxy)carbonyl]tryptophyl]-L-3-(phenylmethyl)-β-alanine;

(E)-N-[α,β-Didehydro-N-[(tricyclo [3.3.1.1$^{3,7}$]dec-2-yloxy)carbonyl]tryptophyl]-L-3-(phenylmethyl)-β-alanine, Tricyclo[3.3.1.1$^{3,7}$]dec-2-yl (Z)-[1-[1H-indol-3-ylmethylene) -2-oxo-2-[[2-(2-pyridinyl)ethyl]amino]ethyl]carbamate;

(Z)-3-[[2-[2-[[3-(1H-indol-3-yl)-1-oxo-2-[[(tricyclo[3.3.1.1$^{3,7}$]dec-2-yloxy)carbonyl]amino]-2-propenyl]amino]ethyl]phenyl]amino]-3-oxopropanoic acid; and Methyl (Z) 3-[[2-[2-[[3 (1H-indol-3-yl) 1-oxo-2-[[(tricyclo[3.3.1.1$^{3,7}$]dec-2 -yloxy)carbonyl]amino]-2-propenyl]amino]ethyl]phenyl]amino]-3-oxopropanoate.

The D and the L configurations are possible at the chiral centers and are included in the scope of the invention.

The double bond indicates that the compounds can exist in the E or Z form or as a mixture of these forms.

The compounds include solvates and hydrates and pharmaceutically acceptable salts of the compounds of Formula I.

The compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by conventional methods well known in the art such as conversion to a salt with an optically active compound, followed by separation by chromatography or recrystallization and reconversion to the nonsalt form.

The individual stereoisomers of compounds of the present invention can exist in the E or Z form or as a mixture of the E and Z forms. The E and Z stereoisomers may be separated from mixtures of the stereoisomers by conventional techniques such as column chromatography or repetitive recrystallizations.

Scheme I below summarizes the synthesis of intermediates and final products of the instant invention.

The compounds of the instant invention are made as fully described in the examples and the scheme. Other references describing known procedures are: D. Barton and W. D. Ollis, eds., *Comprehensive Organic Chemistry*, Chap. 22, pp 121–169, G. H. Whitham; V. Schmidt, A. Liberknecht, J. Wild, *Synthesis* 159, 1989; C. H. Stammer, *Chemistry and Biochemistry of Amino Acids, Peptides and Proteins*, Vol. 6, Chap. 2, pp 33–74, 1982, publishers J. Wright & Sons Ltd., London.

SCHEME I

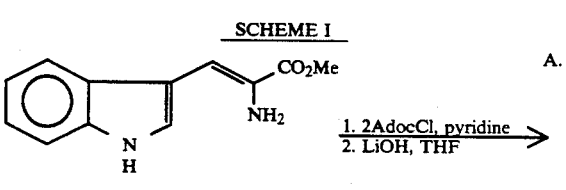

Ref: JOC 1979, 44, 3741

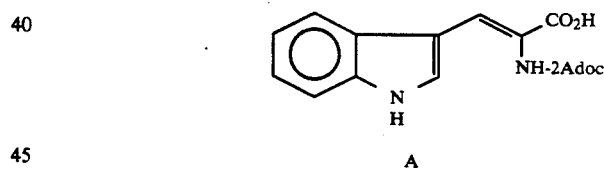

A

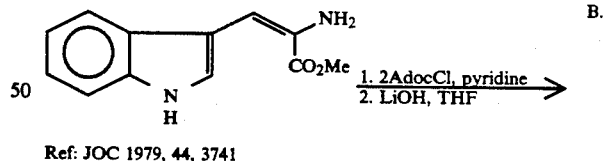

Ref: JOC 1979, 44, 3741

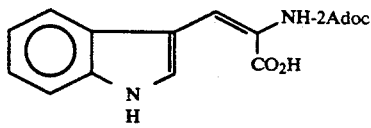

B

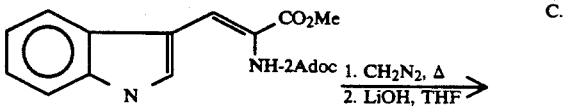

Ref: JOC 1985, 30, 3167

-continued
SCHEME I

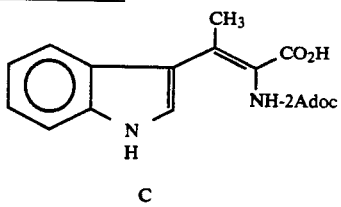

C

Intermediates A, B, and C are then coupled to the phenethylamides using active ester methodology:

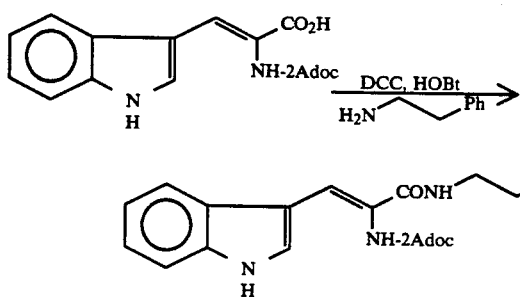

The biological activity of compounds of the present invention was evaluated employing an initial screening test which rapidly and accurately measured the binding of the tested compound to known CCK receptor sites. Specific CCK receptors have been shown to exist in the central nervous system. (See Hays, et al, *Neuropeptides* 1:53–62, 1980; and Satuer et al, *Science* 208:1155–1156, 1980.)

In this screening test, the cerebral cortices taken from male CFLP mice weighing between 30 to 40 g were dissected on ice, weighed, and homogenized in 10 volumes of 50 mM Tris-HCl buffer (pH 7.4 at 0°–4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM $MgCl_2$, 1 nM EDTA, 5 mg/mL bovine albumin, and bacitracin (0.25 mg/mL).

In saturation studies, cerebral cortical membranes were incubated at 23° C. for 120 minutes in a final volume of 500 μL of Hepes incubation buffer (pH 7.2) together with 0.2–20 nM tritiated-pentagastrin (Amersham International, England).

In the displacement experiments, membranes were incubated with a single concentration (2 nM) of ligand, together with increasing concentrations ($10^{11}$ to $10^{-4}$M) of competitive test compound. In each case, the nonspecific binding was defined as that persisting in the presence of the unlabeled octapeptide CCK26-33 ($10^{-6}$M).

Following incubation, radioactivity bound to membranes was separated from that free in solution by rapid filtration through Whatman GF/B filters and washed three times with 4 mL of ice cold Tris-HCl buffer. Filters from samples incubated with tritiated pentagastrin were placed in polyethylene vials with 4 mL of scintillation cocktail, and the radioactivity was estimated by liquid scintillation spectrometry (efficiency 47% to 52%).

The specific binding to CCK receptor sites was defined as the total bound tritiated-pentagastrin minus the amount of tritiated-pentagastrin bound in the presence of $10^{-6}$ octapeptide, CCK26-33.

Saturation curves for specific tritiated-pentagastrin binding to mouse cortical membranes were analyzed by the methods of Scatchard (*Ann. New York Acad. Sci.* 51:660–672, 1949), and Hill (*J. Physiol.* 40:IV–VIII, 1910), to provide estimates for the maximum number of binding sites ($B_{max}$) and the equilibrium dissociation constant ($K_a$).

In displacement experiments, inhibition curves were analyzed by either logit-log plots or the iterative curve fitting computer program ALLFIT (DeLean, Munson, and Redbard, 1978) to provide estimates of the $IC_{50}$ and nH (apparent Hill coefficient values). ($IC_{50}$ values were defined as the concentration of test compound required to produce 50% inhibition of specific binding.)

The inhibition constant ($K_i$) of the test compound was then calculated according to the Cheng Prusoff equation:

$$K_i = \frac{IC_{50}}{1 + [L]/K_a}$$

where [L] is the concentration of radiolabel and $K_a$ is the equilibrium dissociation constant.

The $K_i$/M values for several representative compounds of the present invention are present in Table 1.

TABLE 1

| Example Number | Binding to Central CCK-B Receptors[a] | |
|---|---|---|
| | $K_i$ (nM) | (n)[b] |
| 1 | 1520 | 1 |
| 2 | 13 | 4 |
| 3 | 507 | 3 |
| 4, | 616 | 2 |
| step 2 | | |
| 4 | 209 | 2 |
| 5 | 0.3 | 2 |

[a]Binding affinity protocol Horwell, et al, J. Med. Chem. 34:404, 1991.
[b]Number of assays performed Table 1 above summarizes the binding of several illustrative compounds of the invention to central CCK-B receptors.

Anxiolytic activity is assessed in the light/dark exploration test in the mouse (B. J. Jones, et al, *Br. J. Pharmacol.* 93:985–993, 1988).

The number of mice is 5 and the pretreatment time is 40 minutes. The compound is given PO in 0.1-, 1-, and 10-mg/kg doses.

The apparatus is an open-topped box, 45 cm long, 27 cm wide, and 27 cm high, divided into a small (2/5) area and a large (3/5) area by a partition that extends 20 cm above the walls. There is a 7.5×7.5 cm opening in the partition at floor level. The small compartment is painted black and the large compartment white. The floor of each compartment is marked into 9 cm squares. The white compartment is illuminated by a 100-watt tungsten bulb 17 cm above the box and the black compartment by a similarly placed 60-watt red bulb. The laboratory is illuminated with red light.

All tests are performed between 13 hundred hours 0 minutes and 18 hundred hours 0 minutes. Each mouse is tested by placing it in the center of the white area and allowing it to explore the novel environment for 5 minutes. Its behavior is recorded on videotape and the behavioral analysis is performed subsequently from the recording. Five parameters are measured: the latency to entry into the dark compartment, the time spent in each area, the number of transitions between compartments, the number of lines crossed in each compartment, and the number of rears in each compartment.

In this test an increase in the time spent in the white area is a sensitive measure of the anxiolytic effects of several standard anxiolytic drugs. Drugs are dissolved in water or saline and administered either subcutaneously, intraperitoneally, or by mouth (PO) via a stomach needle.

The compounds of the instant invention are useful as antipsychotic agents. The compounds are tested for their ability to reduce the effects of intra-accumbens amphetamine in the rat as described hereinafter.

Male Sprague Dawley (CD) Bradford strain rats are used. The rats are housed in groups of five at a temperature of 21°±2° C. on a 12-hour light-dark cycle of lights-on between 07 hours 00 minutes and 20 hours 00 minutes. Rats are fed CRM diet (Labsure) and allowed water ad libitum.

Rats are anesthetized with chloral hydrate (400 mg/kg$^{-1}$ SC) and placed in a Kopf stereotaxic frame. Chronically indwelling guide cannulae (constructed of stainless steel tubing 0.65 mm diameter held bilaterally on Parspex holders) are implanted using standard stereotaxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert. −1.8, lat. ±4.5) (atlas of De Groot, 1959). The guides are kept patent during a 14 day recovery period using stainless steel stylets, 0.3 mm diameter, which extend 0.5 mm beyond the guide tips.

Rats are manually restrained and the stylets removed. Intracerebral injection cannulae, 0.3 mm diameter, are inserted and drugs delivered in a volume of 0.5 μL over 5 seconds (a further 55 seconds is allowed for deposition) from Hamilton syringes attached via polythene tubing to the injection units. Animals are used on a single occasion only.

Behavioral experiments are conducted between 07 hours 30 minutes and 21 hours 30 minutes in a quiet room maintained at 22°±2° C. Rats are taken from the holding room and allowed 1 hour to adapt to the new environment. Locomotor activity is assessed in individual screened Perspex cages (25×15×15 cm (high) (banked in groups of 30), each fitted with one photocell unit along the longer axis 3.5 cm from the side; this position has been found to minimize spurious activity counts due to, for example, preening and head movements when the animal is stationary. Interruptions of the light beam are recorded every 5 minutes. At this time, animals are also observed for the presence of any nonspecific change in locomotor activity, e.g., sedation, prostration, stereotyped movements, that can interfere with the recording of locomotor activity.

The abilities of the compounds (20) and (20A) to inhibit the hyperactivity caused by the injection of amphetamine into the nucleus accumbens of the rat is measured.

An increase in locomotor activity followed the bilateral injection of amphetamine (20 μg) into the nucleus accumbens; peak hyperactivity (50 to 60 counts 5 minutes$^{-1}$) occurs 20 to 40 minutes after injection.

Intraperitoneal injection of the rats with a test compound (20 mg/kg or 30 mg/kg) reduces the hyperactivity caused by the intra-accumbens injection of amphetamine. This test is known to be predictive of antipsychotic activity (Costall, Domeney & Naylor & Tyers, (*Brit. 5 Pharmac.* 92:881–894).

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

Examples 1 to 4 are illustrative of methods of preparing compounds of the invention. They are not intended to limit the scope of the invention in any way.

EXAMPLE 1

Carbamic acid,
[1-(1H-indol-3-ylmethylene)-2-oxo-2-[(2-phenylethyl)amino]ethyl]-, tricyclo[3.3.1.1$^{3,7}$]dec-2-yl ester, (Z)-

Step 1

To a stirred suspension of RS-serine methylester hydrochloride (2.0 g, 12.86 mmol) and 2-adamantylchloroformate (4.14 g, 19.28 mmol) in anhydrous THF (25 mL) at room temperature was added a solution of triethylamine (5.0 mL, 35.35 mmol) in anhydrous THF (25 mL) over 15 minutes. After stirring at room temperature for 20 hours, the mixture was filtered and diluted with Et$_2$O (25 mL). The Et$_2$O solution was washed with 5% citric acid solution (2×25 mL) and brine (25 mL). The Et$_2$O solution was dried over MgSO$_4$, filtered, and the solvent removed in vacuo. The residue was purified by chromatography on silica using 67% n-hexane/33% EtOAc, then 50% n-hexane/50% EtOAc as eluant, giving the product as a white solid (1.30 g, 34%); mp 73°-74° C.; IR (film) 3419, 1747, and 1698 cm$^{-1}$; δ NMR (CDCl$_3$) 1.53-1.58 (2H, m), 1.73-1.87 (8H, m), 2.02-2.10 (4H, m), 2.85 (1H, b), 3.79 (3H, s), 3.89-4.08 (2H, m), 4.43 (1H, b), 4.82 (1H, s), 5.73 (1H, d, J 7.6 Hz); Anal. (C$_{15}$H$_{23}$NO$_5$) C, H, N.

Step 2

To a stirred solution of the methylester (0.297 g, 1.0 mmol) in CH$_3$CN (5 mL) was added disuccinimidylcarbonate (0.256 g, 1.0 mmol) followed by triethylamine (0.139 mL, 1.0 mmol). The resulting colorless solution was stirred at room temperature for 20 hours and the solvent removed in vacuo. The residue was dissolved in EtOAc (25 mL) and washed with 5% citric acid solution (2×25 mL) and brine (25 mL). The EtOAc solution was dried over MgSO$_4$, filtered, and the solvent removed in vacuo. The residue was purified by chromatography on silica using CH$_2$Cl$_2$ as eluant, which gave the product (0.151 g, 56%) as a syrup; IR (film) 1716 cm$^{-1}$; δNMR (CDCl$_3$) 1.55-1.58 (2H, m), 1.74-1.89 (8H, m), 2.00-2.04 (4H, m), 3.85 (3H, s), 4.88 (1H, s), 5.76 (1H, s), 6.22 (1H, s), 7.17 (1H, b).

Step 3

N-tosylindole (0.305 g, 1.12 mmol), the methylester (0.628 g, 2.25 mmol), palladium(II)chloride (0.199 g, 1.12 mmol), and anhydrous sodium acetate (0.368 g, 4.48 mmol) in acetic acid (10 mL) were heated at 130° C. for 2 hours. To the cooled mixture was added Et$_2$O (50 mL), which was then filtered through celite. The brown solution was washed with aqueous 1N NaOH solution (3×50 mL) and brine (50 mL). The Et$_2$O solution was dried over MgSO$_4$, filtered, and the solvent removed in vacuo. The residue was purified by chromatography on silica using 67% n-hexane/33% EtOAc as eluant which gave the product (0.282 g, 46%) as a yellow solid, mp 146.5°-151.5° C.; IR (film) 1708 cm$^{-1}$; δNMR (CDCl$_3$) 1.52-2.04 (14H, m), 2.33 (3H, s), 3.86 (3H, s), 4.87 (1H, s), 6.44 (1H, b), 7.20-7.33 (4H, m), 7.57 (1H, s), 7.64-7.67 (1H, m), 7.77 (1H, d, J 8.3 Hz), 7.90 (1H, s), 7.95 (1H, d, J 7.9 Hz); Anal. (C$_{30}$H$_{32}$N$_2$O$_6$S) C, H, N, S.

Step 4

A solution of the tosylester (0.175 g, 0.32 mmol) in MeOH (10 mL) was refluxed with potassium hydroxide (0.284 g, 5.07 mmol) for 12 hours. After cooling, aqueous 1N HCl (5.5 mL, 5.5 mmol) was added and the mixture diluted with water (20 mL) and extracted once with Et$_2$O (25 mL). The Et$_2$O solution was dried over MgSO$_4$, filtered, and the solvent removed in vacuo. Recrystallization from 50% EtOAc/50% n-hexane gave the product as a tan solid (0.044 g, 36%); mp 221°-227° C.; IR (film) 1693 cm$^{-1}$; δNMR (DMSO-d$_6$) 1.20-2.20 (14H, m), 4.68 (1H, s), 7.09-7.20 (2H, m), 7.45 (1H, d, J 7.8 Hz), 7.67 (1H, s), 7.73-7.80 (2H, m), 8.52 (1H, b), 11.72 (1H, s), 12.28 (1H, s); Anal. (C$_{22}$H$_{24}$N$_2$O$_4$.0.75H$_2$O) C, H, N.

Step 5

To a stirred solution of the acid (0.030 g, 0.08 mmol) and 1-hydroxybenzotriazole hydrate (0.015 g, 0.10 mmol) in EtOAc (10 mL) at room temperature was added N,N'-dicyclohexylcarbodiimide (0.019 g, 0.09 mmol) and the mixture stirred for 2 hours. A solution of 2-phenethylamine (0.015 g, 0.12 mmol) in EtOAc (1 mL) was added and the mixture stirred at room temperature for 21 hours. The N,N'- dicyclohexylurea was filtered off and the solvent removed in vacuo. The yellow residue was purified by chromatography on silica using 67% EtOAc/33% n-hexane as eluant, giving the product as an off white solid (0.021 g, 54%); mp 92°-99° C.; IR (film) 1706, 1651, and 1607 cm$^{-1}$; δNMR (CDCl$_3$) 1.62-1.91 (14H, m), 2.89 (2H, t, J 7.1 Hz), 3.61-3.68 (2H, m), 4.85 (1H, s), 5.80 (1H, b), 6.43 (1H, b), 7.17-7.40 (8H, m), 7.53 (1H, s), 7.74-7.76 (2H, m), 8.78 (1H, s); Anal. (C$_{30}$H$_{33}$N$_3$O$_3$.1.0 H$_2$O) C, H, N.

EXAMPLE 2

(Z)-N-[α,β-Didehydro-N-[(tricyclo[3.3.1.1$^{3,7}$]dec-2-yloxy)carbonyl]tryptophyl]-L-3-(phenylmethyl)-β-alanine

Step 1

A stirred solution of the acid (0.266 g, 0.70 mmol) in DMF (1 mL) was diluted with EtOAc (25 mL). 1-Hydroxybenzotriazole monohydrate (0.134 g, 0.88 mmol) was added followed by N,N'-dicyclohexylcarbodiimide (0.159 g, 0.77 mmol) and the solution stirred at room temperature for 2 hours. The amino ester hydrochloride (0.20 g, 0.87 mmol) was added, followed by a solution of triethylamine (0.121 mL, 0.87 mmol) in EtOAc (20 mL) added dropwise over 10 minutes and the mixture stirred at room temperature for 72 hours. The N,N'-dicyclohexylurea was filtered off and the EtOAc solution washed with aqueous 5% citric acid solution (2×25 mL), aqueous saturated NaHCO$_3$ (2×25 mL), aqueous 5% citric acid solution (25 mL), and brine (25 mL). The EtOAc was dried over MgSO$_4$, filtered, and the solvent removed in vacuo. The residue was purified by chromatography on silica using 50% n-hexane/50% EtOAc as eluant, giving the product as a tan solid (0.252 g, 65%), mp 92°-107° C.; [α]$_D^{20}$ −23.5° (c=0.10, CHCl$_3$); IR (film) 3310, 2907, 1722, 1704, and 1654 cm$^{-1}$; δNMR (CDCl$_3$) 1.28-2.04 (14H m) 2.56 (2H, d, J 5.2 Hz), 2.88 (1H, dd, J 13.5, 8.4 Hz), 3.05 (1H, dd, J 13.6, 5.8 Hz), 3.69 (3H, s), 4.60-4.68 (1H, m), 4.86 (1H, s), 5.94 (1H, b), 7.10-7.33 (8H, m), 7.39 (1H, d, J 7.4 Hz), 7.57 (1H, s), 7.75-7.77 (2H, m), 8.82 (1H, b); Anal. (C$_{33}$H$_{37}$N$_3$O$_5$) C, H, N.

Step 2

To a stirred solution of the methylester (0.178 g, 0.32 mmol) in THF (20 mL) at 0° C. was added dropwise over 30 minutes a solution of aqueous 0.1N LiOH (3.5 mL, 0.35 mmol) diluted with water (6.5 mL). The cold solution was stirred with slow rewarming to room temperature for 21 hours. The solvent was removed in vacuo and the residue diluted with water (10 mL) and extracted once with Et₂O (50 mL). The aqueous solution was made pH 5 with aqueous 0.1N HCl and extracted with EtOAc (2×25 mL). The EtOAc solution was dried over MgSO₄, filtered, and the solvent removed in vacuo, giving the product as a white solid (0.071 g, 41%); mp 157°-168° C.; $[\alpha]_D^{20}$ −54.8° (c=0.10, CHCl₃); IR (film) 1696 and 1651 cm⁻¹; δNMR (DMSO-d⁶) 1.34–1.50 (2H, m), 1.68–1.99 (12H, m), 2.38–2.55 (2H, m), 2.84 (1H, dd, J 13.6, 6.4 Hz), 2.95 (1H, dd, J 13.5, 7.1 Hz), 4.37–4.44 (1H, m), 4.69 (1H, s), 7.09–7.32 (7H, m), 7.41–7.45 (2H, m), 7.58 (1H, d, J 8.3 Hz), 7.66–7.72 (2H, m), 8.15 (1H, s), 11.45 (1H, s); Anal. (C₃₂H₃₅N₃O₅.0.5H₂O) C, H, N.

EXAMPLE 3

Tricyclo[3.3.1.1³,⁷]dec-2-yl (Z)-[1-(1H-indol-3-ylmethylene) -2-oxo-2-[[2-(2-pyridinyl)ethyl]amino]ethyl]carbamate

Step 1

A stirred solution of the acid (0.140 g, 0.37 mmol) in DMF (1 mL) was diluted with EtOAc (25 mL). 1-Hydroxybenzotriazole monohydrate (0.068 g, 0.44 mmol) was added followed by N,N'-dicyclohexylcarbodiimide (0.091 g, 0.44 mmol) and the mixture stirred at room temperature for 2 hours. A solution of 2-(2'-aminoethyl)pyridine (0.068 g, 0.56 mmol) in EtOAc (5 mL) was added dropwise over 15 minutes and the mixture stirred at room temperature for 21 hours. The N,N'-dicyclohexylurea was filtered off and the EtOAc solution washed with water (25 mL), dried over MgSO₄, filtered, and the solvent removed in vacuo. The residue was purified by chromatography on silica using EtOAc then 2% MeOH/98% EtOAc as eluants, giving the product as a white solid (0.126 g, 70%); mp 188°-200° C.; IR (film) 3238, 2908, 1703, and 1655 cm⁻¹; δNMR (CDCl₃) 1.28–2.04 (14H, m), 3.04–3.08 (2H, t, J 6.3 Hz), 3.76–3.82 (2H, m), 4.79 (1H, s), 6.06 (1H, b), 7.13–7.28 (4H, m), 7.39 (1H, d, J 7.5 Hz), 7.59–7.78 (5H, m), 8.54 (1H, d, J 4.3 Hz), 9.02 (1H, s); Anal. (C₂₉H₃₂N₄O₃) C, H, N.

EXAMPLE 4

(Z)-3-[[2-[2-[[3-(1H-indol-3-yl)-1-oxo-2-[[(tricyclo[3.3.1.1³,⁷]dec-2-yloxy)carbonyl]amino]-2-propenyl]amino]ethyl]phenyl]amino]-3-oxopropanoic acid

Step 1

A stirred solution of the acid (0.380 g, 1.0 mmol) in DMF (1 mL) was diluted with EtOAc (25 mL). 1-Hydroxybenzotriazole monohydrate (0.184 g, 1.2 mmol) was added followed by N,N'-dicyclohexylcarbodiimide (0.248 g, 1.2 mmol) and the mixture stirred for 2 hours at room temperature. A solution of the diamine (0.161 g, 1.18 mmol) in EtOAc (5 mL) was added dropwise over 20 minutes and the mixture stirred at room temperature for 18 hours. The N,N'-dicyclohexylurea was filtered off and the EtOAc solution washed with water (2×25 mL), dried over MgSO₄, filtered, and the solvent removed in vacuo. The residue was purified by chromatography on silica using 2% MeOH/98% CH₂Cl₂ as eluant, giving the product as a tan solid (0.166 g, 33%); mp 112°-120.5° C.; IR (film) 3349, 1702, 1651, and 1605 cm⁻¹; δNMR (DMSO-d₆) 1.50–2.30(14H, m), 2.62 (2H, t, J 8.3 Hz), 3.28–3.31 (2H, m), 4.69 (1H, s), 5.12 (2H, s), 6.45–6.50 (1H, m), 6.62 (1H, d, J 8.4 Hz), 6.89–6.93 (2H, m), 7.09–7.19 (2H, m), 7.43 (1H, d, J 7.6 Hz), 7.55 (1H, s), 7.70 (1H, s), 7.75 (1H, d, J 7.7 Hz), 8.06–8.56 (2H, m), 11.68 (1H, s); Anal. (C₃₀H₃₄N₄O₃.0.3H₂O) C, H, N.

Methyl (Z)-3-[[2-2-[[3-(1H-indol-3-yl)-1-oxo-2-[[(tricyclo[3.3.1.1³,⁷]dec-2-yloxy)carbonyl]amino]-2-propenyl]amino]ethyl]phenyl]amino]-3-oxopropanoate

Step 2

To a stirred solution of the amine (0.10 g, 0.20 mmol) and triethylamine (0.031 mL, 0.22 mmol) in anhydrous THF (10 mL) at 0° C. was added a solution of methylmalonylchloride (0.026 mL, 0.24 mmol) in anhydrous THF (2 mL) dropwise over 5 minutes. The cold solution was stirred with slow rewarming to room temperature over 24 hours. The mixture was diluted with Et₂O (25 mL) and washed with aqueous 5% citric acid solution (2×25 mL) and brine (25 mL). The Et₂O solution was dried over MgSO₄, filtered, and the solvent removed in vacuo. The residue was purified by chromatography on silica using 67% EtOAc/33% n-hexane as eluant, giving the product as a white solid (0.070 g, 58%); mp 111°-115° C.; IR (film) 3263, 1704, and 1652 cm⁻¹; δNMR (CDCl₃) 1.30–2.06 (14H, m), 2.83–2.88 (2H, m), 3.32–3.48 (2H, m), 3.72 (3H, s), 3.75 (2H, s), 4.83 (1H, s), 6.15 (1H, s), 6.90–7.23 (6H, m), 7.36 (1H, d, J 7.0 Hz), 7.54 (1H, s), 7.75–7.85 (2H, m), 8.04 (1H, b), 9.16 (1H, b), 9.77 (1H, b); Anal. (C₃₄H₃₈N₄O₆.0.25H₂O) C, H, N.

Step 3

To a stirred solution of the methylester (0.033 g, 0.055 mmol) in THF (7 mL) at 0° C. was added dropwise over 1.75 hours a solution of aqueous 0.01N LiOH solution (6.6 mL, 0.066 mmol). The cold solution was stirred with slow rewarming to room temperature for 28 hours. The solvent was removed in vacuo and the residue diluted with water (10 mL) and extracted once with Et₂O (20 mL). The aqueous solution was made pH 5 with aqueous 0.1N HCl and extracted with EtOAc (2×20 mL). The EtOAc was dried over MgSO₄, filtered, and the solvent removed in vacuo to give the product as a tan solid (0.021 g, 66%); mp 106°-126° C.; IR (film) 3262, 1705, and 1650 cm⁻¹; δNMR (DMSO-d₆) 1.49–1.99 (14H, m), 2.84 (2H, t, J 7.6 Hz), 3.36–3.44 (2H, m), 3.51 (2H, s), 4.71 (1H, s), 7.09–7.27 (5H, m), 7.43 (1H, d, J 7.4 Hz), 7.55 (1H, s), 7.64–7.75 (3H, m), 7.90 (1H, b), 8.17 (1H, b), 9.68 (1H, s), 11.49 (1H, s), 12.25 (1H, b); Anal. (C₃₃H₃₆N₄O₆.1.0H₂O.0.5CH₃CO₂Et) C, H, N.

EXAMPLE 5

(E/Z)-N-[α,β-Didehydro-N-[(tricyclo[3.3.1.1³,⁷]dec-2-yloxy)carbonyl]tryptophyl]-L-3-(phenylmethyl)-β-alanine

Step 1

A solution of the acid from Example 2 (0.116 g, 0.21 mmol) in CH₃CN (10 mL) was degassed with N₂ for 1 hour. This solution was then irradiated for 12 hours at 350 nm under a stream of N₂. The solvent was removed in vacuo and the residue purified by reverse phase chromatography on silica using 75% MeOH/25% H₂O as eluant, giving the product as a white solid (0.017 g, 21%) (HPLC of the product indicated that it was a mixture containing 65% Z isomer and 35% E isomer); IR (film) 3342, 2918, 1709, and 1649 cm$^{-1}$; δNMR (CDCl$_3$) 1.26-2.06 (14H, m), 2.38-2.70 (2H, m), 2.85-3.08 (2H, m), 4.36-4.70 (1H, m), 4.81, 4.89 (1H, 2s), 6.94-7.65 (13H, m), 9.0, 9.25 (1H, 2s); Anal. (C$_{32}$H$_{35}$N$_3$O$_5$·1.25H$_2$O) C, H, N.

We claim:

1. A compound of formula

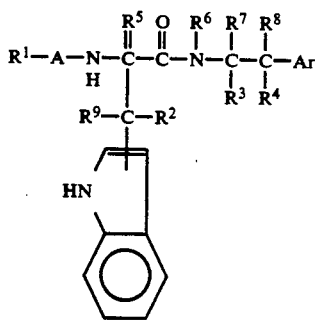

or a pharmaceutically acceptable salt thereof wherein

R$_1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, CO$_2$R*, CF$_3$, NR$^{11}$R$^{12}$, and —(CH$_2$)$_n$OR$^{11}$ wherein R* is hydrogen or a straight or branched alkyl of from one to six carbon atoms, R$^{11}$ and R$^{12}$ are each independently hydrogen or alkyl of from one to about six carbon atoms and n is an integer of from zero to six;

A is —(CH$_2$)$_n$CO—, —SO$_2$—, —NHCO—, or —O(CH$_2$)$_n$CO— wherein n is an integer of from 0 to 6;

R$^2$ and R$^5$ are taken together to form a double bond or to form a ring —(CH$_2$)$_m$X(CH$_2$)$_n$ wherein m is an integer of from 0 to 5, n is as defined above, wherein m and n cannot both be 0 and the sum of m and n is not greater than 8, X is a bond, —N=N— or a heteroatom selected from O, S, or N;

R$^3$ and R$^4$ are each independently hydrogen or —(CH$_2$)$_{n'}$-B-D wherein
n' is an integer of from zero to 3,
B is a bond or —OCO(CH$_2$)$_n$—, —O(CH$_2$)$_n$—, —NHCO(CH$_2$)$_n$—, —CONH(CH$_2$)$_n$—, —NH-COCH=CH—, or —COO(CH$_2$)$_n$— wherein n is as defined above, and
D is —COOR$^{10}$, —CONH$_2$, —CH, —NH$_2$, —OH, or —H wherein R$^{10}$ is hydrogen or a straight or branched alkyl of from 1 to 6 carbon atoms or —(CH$_2$)$_n$CO$_2$H;

R$^6$ is hydrogen or a straight or branched alkyl of from 1 to 6 carbon atoms or —(CH$_2$)$_n$CO$_2$H;

R$^7$ and R$^8$ are each independently hydrogen, or can together form a doubly bonded moiety; and R$^9$ is hydrogen, —C≡N, —CO$_2$R$_{10}$, —R$_{10}$, —NR$_{10}$R$_6$, —SR$_{10}$ wherein R$_{10}$ is as defined above;

Ar is a phenyl, phenyl substituted by halogen, pyridinyl or cyclohexyl moiety.

2. A compound of claim 1 wherein
R$^1$ is adamantyl, endobornyl, methylcyclohexyl, or cyclooctyl;
A is —OCO—, —NHCO—, or —(CH$_2$)$_n$CO—;

R$^2$ and R$^5$ are taken together to form cyclopropyl or a double bond;

R$^6$ is hydrogen or CH$_2$CO$_2$H;

R$^3$ and R$^4$ are each independently selected from CH$_2$CO$_2$H, NHCO(CH$_2$)$_n$CO$_2$H, (CH$_2$)$_n$NHCOCH=CHCO$_2$H, CH$_2$S(O)$_p$CH$_2$CO$_2$H, wherein p is an integer of from 0 to 2, and n is as defined above;

R$^7$ and R$^8$ are each independently hydrogen or together form a doubly bonded moiety;

R$^9$ is hydrogen, —C≡N, —CO$_2$C$_2$H$_5$, or —CH$_3$;

Ar is phenyl, phenyl substituted by halogen, pyridinyl, or cyclohexyl.

3. A compound according to claim 1 wherein
R$^1$ is 2-adamantyl, 1-S-endobornyl, or 2-methylcyclohexyl;
A is —OCO— or —NHCO—;
R$^2$ and R$^5$ taken together form a double bond;
R$^3$ and R$^4$ are each independently hydrogen, CH$_2$CO$_2$H, NHCO(CH$_2$)$_2$CO$_2$H, or CH$_2$NHCOCH=CHCO$_2$H;
R$^6$ is hydrogen;
R$^7$ and R$^8$ are hydrogen or taken together form a double bond;
R$^9$ is hydrogen, methyl, or C≡N; and
Ar is phenyl or pyridinyl.

4. A compound according to claim 1 selected from:

Carbamic acid, [1-(1H indol-3-ylmethylene) -2-oxo-2-[(2-phenylethyl)amino]ethyl]-, tricyclo[3.3.1.1$^{3,7}$]dec-2-yl ester, (Z)-;

(Z)-N-[α,β-Didehydro-N-[(tricyclo[3.3.1.1$^{3,7}$]dec-2-yloxy)carbonyl]tryptophyl]-L -3-(phenylmethyl)-β-alanine;

(E)-N-[α,β-Didehydro-N-[(tricyclo[3.3.1.1$^{3,7}$]dec-2-yloxy)carbonyl]tryptophyl]-L -3-(phenylmethyl)-β-alanine;

Tricyclo[3.3.1.1$^{3,7}$]dec-2-yl (Z)-[1-(1H -indol-3-ylmethylene)-2-oxo-2-[[2-(2-pyridinyl)ethyl]amino]ethyl]-carbamate;

(Z)-3-[[2-[2-[[3-(1H-indol-3-yl)-1-oxo-2-[[(tricyclo[3.3.1.1$^{3,7}$]dec-2-yloxy)carbonyl]amino]-3-oxopropanoic acid; and Methyl (Z)-3-[[2-[2-[[3-(1H-indol-3-yl)1-oxo-2-[[(tricyclo[3.3.1.1$^{3,7}$]dec-2-yloxy) carbonyl]amino]-2-propenyl]amino]ethyl]phenyl]amino]-3-oxopropanoate.

5. A pharmaceutical composition for use in the treatment of anxiety comprising an anxiolytically effective amount of at least one compound of claim 1 or a pharmaceutically acceptable salt thereof in combination with a pharmaceutically acceptable carrier.

6. A method of treating anxiety in a human in need of such treatment which comprises administering a composition according to claim 5 to said human.

7. A pharmaceutical composition for use in the treatment of psychoses comprising an antipsychotically effective amount of at least one compound of claim 1 or a pharmaceutically acceptable salt thereof in combination with a pharmaceutically acceptable carrier.

8. A method for treating psychoses in a human in need of such treatment which comprises administering a composition according to claim 7 to said human.

9. A pharmaceutical composition for use in reducing gastric acid secretion comprising a therapeutically effective amount of a least one compound of claim 1 or a pharmaceutically acceptable salt thereof in combination with a pharmaceutically acceptable carrier.

10. A method for reducing gastric acid secretion in a human in need of such treatment which comprises administering a composition according to claim 9 to said human.

11. A pharmaceutical composition for use in treating the symptoms of cognitive decline comprising a therapeutically effective amount of at least one compound of claim 1 or a pharmaceutically acceptable salt thereof in combination with a pharmaceutically acceptable carrier.

* * * * *

UNITED STATES PATENT AND TRADEMARK OFFICE
CERTIFICATE OF CORRECTION

PATENT NO. : 5,218,123
DATED : June 8, 1993
INVENTOR(S) : Horwell, et al

It is certified that error appears in the above-indentified patent and that said Letters Patent is hereby corrected as shown below:

Column 2, line 53, delete the double bond between the carbon and the $R^5$ and insert a single bond.

Column 4, line 7, delete the double bond between the carbon and the $R^5$ and insert a single bond.

Column 15, line 11, delete the double bond between the carbon and the $R^5$ and insert a single bond.

Column 15, line 53, delete "-CH," and insert instead "-CN,"

Column 16, line 42, after the "amino]" and before "-3-" insert "-2-propenyl]amino]ethyl]phenyl]amino]"

Signed and Sealed this

Eleventh Day of January, 1994

Attest:

BRUCE LEHMAN

Attesting Officer    Commissioner of Patents and Trademarks